United States Patent
Lee et al.

(10) Patent No.: US 10,926,213 B2
(45) Date of Patent: Feb. 23, 2021

(54) SULFUR DIOXIDE ABSORBENT IS AN IONIC LIQUID INCLUDING A SALT OF A DIAMINE COMPOUND THAT IS SUBSTITUTED WITH A HYDROXYL GROUP

(71) Applicant: KOREA INSTITUTE OF SCIENCE AND TECHNOLOGY, Seoul (KR)

(72) Inventors: Hyun Joo Lee, Seoul (KR); Ung Lee, Seoul (KR); Hong Gon Kim, Seoul (KR); Shinhye Cho, Seoul (KR); He Won Lee, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 16/454,566

(22) Filed: Jun. 27, 2019

(65) Prior Publication Data
US 2020/0155997 A1    May 21, 2020

(30) Foreign Application Priority Data
Nov. 20, 2018 (KR) .................. 10-2018-0143845

(51) Int. Cl.
| C07D 487/08 | (2006.01) |
| B01D 53/14 | (2006.01) |
| B01D 53/50 | (2006.01) |
| B01D 53/78 | (2006.01) |
| C07C 215/40 | (2006.01) |
| C07D 241/04 | (2006.01) |

(52) U.S. Cl.
CPC ..... *B01D 53/1493* (2013.01); *B01D 53/1481* (2013.01); *B01D 53/507* (2013.01); *B01D 53/78* (2013.01); *C07C 215/40* (2013.01); *C07D 241/04* (2013.01); *C07D 487/08* (2013.01); *B01D 2252/2041* (2013.01); *B01D 2252/20431* (2013.01); *B01D 2252/20447* (2013.01); *B01D 2252/20484* (2013.01); *B01D 2252/30* (2013.01)

(58) Field of Classification Search
CPC .... C07D 241/04; C07D 487/08; C07C 215/40
See application file for complete search history.

(56) References Cited

U.S. PATENT DOCUMENTS

| 2,404,854 | A | 12/1944 | Latchum, Jr. et al. |
| 3,904,735 | A | 9/1975 | Atwood et al. |
| 4,201,752 | A | 5/1980 | Kosseim et al. |
| 6,623,659 | B2 | 9/2003 | Munson et al. |
| 6,849,774 | B2 | 2/2005 | Boudreau et al. |
| 2008/0146849 | A1 | 6/2008 | Dai et al. |
| 2008/0271381 | A1* | 11/2008 | Harashina ........ C08G 2/28 51/298 |

FOREIGN PATENT DOCUMENTS

| KR | 10-0831093 B1 | 5/2008 |
| KR | 10-2010-0043796 A | 4/2010 |
| KR | 10-1415844 B1 | 7/2014 |
| KR | 10-1415865 B1 | 7/2014 |

OTHER PUBLICATIONS

PubChem CID 57294404 (2012).*
PubChem CID 12293659 (2007).*
PubChem CID 53705908 (2011).*
Weize Wu et al., "Desulfurization of Flue Gas: $SO_2$ Absorption by an Ionic Liquid", Angew. Chem. Int. Ed., 2004, pp. 2415-2417, vol. 43.
Sung Yun Hong et al., "Ether-functionalized ionic liquids as highly efficient $SO_2$ absorbents", Energy & Environmental Science, 2011, pp. 1802-1806, vol. 4.
Guokai Cui et al., "Highly efficient $SO_2$ capture by dual functionalized ionic liquids through a combination of chemical and physical absorption", Chem. Commun., 2012, pp. 2633-2635, vol. 48.
Luke J. Murphy et al., "Ionic liquids and acid gas capture: water and oxygen as confounding factors", Chem. Commun., 2012, pp. 1227-1229, vol. 48.

* cited by examiner

*Primary Examiner* — Deepak R Rao
(74) *Attorney, Agent, or Firm* — Rabin & Berdo, P.C.

(57) ABSTRACT

A sulfur dioxide absorbent that is an ionic liquid including a solvent; and a salt of a diamine compound that is substituted with a hydroxyl group and has a chemical formula 1 to 3 below dissolved in the solvent:

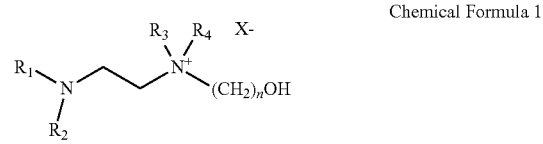

Chemical Formula 1

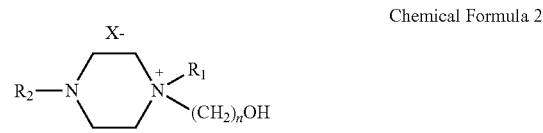

Chemical Formula 2

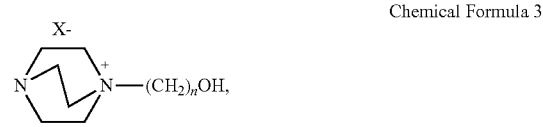

Chemical Formula 3 where, in Chemical Formula 1 and 2, $R_1$-$R_4$ are the same or different and each is independently selected from the group consisting of H, a C1-C6 alkyl, and a C1-C6 alkoxy; and where, in Chemical Formula 1 to 3, X is selected from the group consisting of Cl, Br, I, $MeSO_3$, $CF_3SO_3$, $HCO_2$, $CF_3CO_2$ and $CH_3CO_2$; and n is an integer of 1-10. The sulfur dioxide absorbent is constituted to selectively absorb sulfur dioxide and sulfurous acid ($H_2SO_3$) formed by combination of sulfur dioxide with water, not $CO_2$.

18 Claims, 7 Drawing Sheets

FIG. 7

SULFUR DIOXIDE ABSORBENT IS AN IONIC LIQUID INCLUDING A SALT OF A DIAMINE COMPOUND THAT IS SUBSTITUTED WITH A HYDROXYL GROUP

CROSS-REFERENCE TO RELATED APPLICATIONS

This application claims priority under 35 U.S.C. § 119 to Korean Patent Application No. 10-2018-0143845 filed on Nov. 20, 2018 in the Korean Intellectual Property Office, the disclosure of which is incorporated herein by reference in its entirety.

TECHNICAL FIELD

The present disclosure relates to an absorbent capable of removing not only sulfur dioxide ($SO_2$) contained in combustion exhaust gas or in the air but also sulfurous acid ($H_2SO_3$) formed by combination of sulfur dioxide with water. Particularly, the absorbent uses an ionic liquid in the form of a salt including a diamine compound substituted with a hydroxyl group.

BACKGROUND

In fossil fuel, such as coal and petroleum, a significant amount of sulfur compounds is contained and such sulfur compounds are emitted in the form of sulfur dioxide ($SO_2$) which causes acid rain during production of energy through burning of fuel. Therefore, in most power plants or industrial facilities where fossil fuel is burned, desulfurized exhaust gas is emitted into the air to prevent emission of a main cause of air pollution.

Use of lime (CaO) or limestone ($CaCO_3$) is known as a method for desulfurization of exhaust gas from a power plant. Use of such calcium compounds is advisable in terms of cost efficiency. However, since such calcium compounds have a significantly low solubility to water of about 0.17% (CaO) and about 0.0013% ($CaCO_3$), they are pulverized into very small particles and then formed into slurry in water so that they may react with $SO_2$. Herein, reaction with $SO_2$ is a solid-liquid reaction, and thus does not show a high reaction rate as compared to a liquid-liquid reaction. In addition, use of an excessive amount of water causes a problem related with waste water and such low solubility to water causes a serious problem of pipe blockage during the overall process.

As a liquid $SO_2$ absorbent, an amine-based compound has been used most widely. Particular examples of such absorbents include triethanolamine disclosed in U.S. Pat. No. 3,904,735, monoethanolamine disclosed in U.S. Pat. No. 4,201,752, and diethanolamine disclosed in U.S. Pat. No. 2,404,854. The reason why such an amine absorbent is used as $SO_2$ absorbent is that amine bound chemically with $SO_2$ undergoes a cleavage of binding under heating, and thus $SO_2$ may be desorbed and collected and the absorbent may be regenerated. However, the amine process has the following disadvantages: a high absorbent regeneration temperature caused by strong binding between amine and sulfur dioxide and irreversible decomposition of amine; degradation of performance of the absorbent and supplement of the absorbent; corrosion of an absorption system caused by the amine itself or decomposition products thereof; and contamination of regenerated gas with the vapor pressure of the amine absorbent.

Recently, in order to overcome such disadvantages of the conventional absorbent, there has been an attempt to use an ionic liquid, which shows no volatility, has high thermal and chemical stability and maintains a liquid phase at a low temperature of 100° C., as an absorbent, as disclosed in U.S. Pat. Nos. 6,849,774, 6,623,659, and US Patent Publication No. 2008-0146849.

In addition, according to *Angew. Chem., Int. Ed.* (2004, 43, 2415-2417), use of 1,1,3,3-tetramethylguanidinium lactate ([TMG]L) provides an $SO_2$ absorption ratio of 0.978 mol per mole of ionic liquid. According to Korean Patent No. 10-0831093, [BMIm]Cl provides an $SO_2$ absorption ratio of 1.68 mol per mole of ionic liquid and [EMIm]$EtSO_4$ provides a relatively low $SO_2$ absorption ratio of 0.92 mol per mole of ionic liquid. Further, according to Korean Patent Publication No. 10-2010-0043796, it is reported that a fluorine-containing ionic liquid, [BhFplm]$CF_3CO_2$ (1-butyl-3-hexafluoropropyl imidazolium trifluoroacetate) has high stability against heat and sulfur dioxide and absorbs 0.48 mol of sulfur dioxide per mol of ionic liquid.

However, since an ionic liquid having a fluorine-containing anion, such as tetrafluoroborate ($BF_4$), is decomposed easily by moisture to produce hydrofluoric acid (HF), the ionic liquid as an absorbent may be lost and has a difficulty in regeneration. When the anion is $Cl^-$, the ionic liquid is present in the form of solid at room temperature. Thus, there is a problem in that it is required to maintain the absorption temperature to 50° C. or higher.

*Energy Environ. Sci.*, 4, 1802-1806 (2011) and *Chem. Commun.*, 2633-2635 (2012) discloses a method for increasing absorption ratio of $SO_2$ by using an ionic liquid having an ether functional group or ionic liquid having a tetrazole ion. It is reported that each ionic liquid can absorb $SO_2$ up to 4 mol per mol at 1 bar.

The ionic liquids having such high $SO_2$ absorption ratio are characterized in that a Lewis base site capable of interacting with $SO_2$ having Lewis acid property is present in the molecule. Therefore, molecules having a large number of Lewis base sites per unit molecule show high $SO_2$ absorption ratio.

Meanwhile, exhaust gas includes 5-15% of moisture in addition to $SO_2$. The presence of moisture may be concentrated together with an $SO_2$ absorbent during the treatment of $SO_2$, wherein $SO_2$ reacts with water so that it is converted into a strong acid, $H_2SO_3$. $H_2SO_3$ has quite different chemical properties from $SO_2$. In other words, $H_2SO_3$ does not function as a Lewis acid, and thus it cannot be treated with the conventional $SO_2$ absorbent. On the contrary, when aqueous $H_2SO_3$ solution is treated with a primary to tertiary amine or base, it is possible to isolate $H_2SO_3$ through acid-base reaction. However, in this case, the produced salt is present in a form dissolved in water. As a result, it is required to further carry out separation of the salt from water.

Most of the conventional $SO_2$ absorbents are miscible with water or are decomposed in the presence of water. In addition, absorption ratio of such absorbents for $SO_2$ present in the form of an acid, such as $H_2SO_3$, is not known. In fact, *Chem Commun* 2012, 48, 1227 discloses a method for treating $SO_2$ by using a diethylene triamine/P66614Cl system. Herein, it is stated that when water is present in the ionic liquid or the other amine solvent, acid-base reaction occurs between amine and $H_2SO_3$, not $SO_2$.

REFERENCES

Korean Patent No. 10-0831093
Korean Patent Laid-Open No. 10-2010-0043796

SUMMARY

An embodiment of the present disclosure is directed to providing an absorbent capable of removing not only sulfur dioxide ($SO_2$) contained in combustion exhaust gas or in the air but also sulfurous acid ($H_2SO_3$) formed by combination of sulfur dioxide with water.

Another embodiment of the present disclosure is directed to providing a method for preparing the absorbent.

In one aspect, there is provided a sulfur dioxide absorbent selected from the group consisting of the following [Chemical Formula 1] to [Chemical Formula 3]:

[Chemical Formula 1]

[Chemical Formula 2]

[Chemical Formula 3]

In Chemical Formula 1 to Chemical Formula 3, $R_1$-$R_4$ are the same or different and each is independently selected from the group consisting of H, a C1-C6 alkyl, carbonyl and a C1-C6 alkoxy; X is selected from the group consisting of Cl, Br, I, $MeSO_3$, $CF_3SO_3$, $CF_3CO_2$, $HCO_2$, $CF_3CO_2$ and $CH_3CO_2$; and n is an integer of 1-10.

The sulfur dioxide absorbent may be one that absorbs sulfur dioxide and sulfurous acid ($H_2SO_3$) formed by combination of sulfur dioxide with water.

The sulfur dioxide absorption temperature may be 10-80° C. and the sulfur dioxide desorption temperature may be 50-150° C.

In another aspect, there is provided a method for preparing the sulfur dioxide absorbent, including a step of mixing a compound represented by the following [Chemical Formula 12] with a compound represented by the following [Chemical Formula 15] at a molar ratio of 1:1-5 to form a salt:

[Chemical Formula 12]

[Chemical Formula 15]

In Chemical Formula 12 and Chemical Formula 15, $R_1$-$R_4$ are the same or different and each is independently selected from the group consisting of H, a C1-C6 alkyl, carbonyl and a C1-C6 alkoxy; $Y_1$ is selected from the group consisting of Cl, Br and I; and n is an integer of 1-10.

In a variant, the method may include a step of mixing a compound represented by the following [Chemical Formula 13] with a compound represented by the following [Chemical Formula 15] at a molar ratio of 1:1-5 to form a salt:

[Chemical Formula 13]

[Chemical Formula 15]

$Y_1$—$(CH_2)n$OH

In Chemical Formula 13 and Chemical Formula 15, $R_1$-$R_2$ are the same or different and each is independently selected from the group consisting of H, a C1-C6 alkyl, carbonyl and a C1-C6 alkoxy; $Y_1$ is selected from the group consisting of Cl, Br and I; and n is an integer of 1-10.

In another variant, the method may include a step of mixing a compound represented by the following [Chemical Formula 14] with a compound represented by the following [Chemical Formula 15] at a molar ratio of 1:1-5 to form a salt:

[Chemical Formula 14]

[Chemical Formula 15]

$Y_1$—$(CH_2)n$OH

In Chemical Formula 14 and Chemical Formula 15, $Y_1$ is selected from the group consisting of Cl, Br and I; and n is an integer of 1-10.

According to an embodiment, the salt compound obtained after the completion of the reaction may be reacted with a compound represented by the following [Chemical Formula 16] to exchange the anion of the salt compound:

$MY_2$   [Chemical Formula 16]

In Chemical Formula 16, M is selected from the group consisting of Li, K and Na; and $Y_2$ is selected from the group consisting of $MeSO_3$, $CF_3SO_3$, $CF_3CO_2$, $HCO_2$, $CF_3CO_2$ and $CH_3CO_2$.

According to the present disclosure, a molten salt of a diamine compound substituted with a hydroxyl group is dissolved in a solvent to form an ionic liquid (absorbent). The ionic liquid is used to remove not only sulfur dioxide ($SO_2$) contained in combustion exhaust gas or in the air but also sulfurous acid ($H_2SO_3$) formed by combination of sulfur dioxide with water.

In addition, the sulfur dioxide and sulfurous acid absorbent according to the present disclosure is advantageous in that it shows excellent absorption ratio even at a low $SO_2$ concentration, allows easy desorption of the absorbed $SO_2$, and maintains its absorption ratio to a level similar to the initial absorption ratio without loss even after being used repeatedly. Further, even when the absorbent according to the present disclosure is dissolved in water at a high concentration, it is not solidified, and thus can prevent a pipe blockage phenomenon.

DETAILED DESCRIPTION OF EMBODIMENTS

The present disclosure relates to an absorbent capable of removing not only sulfur dioxide ($SO_2$) contained in combustion exhaust gas or in the air but also sulfurous acid ($H_2SO_3$) formed by combination of sulfur dioxide with water.

The solid-based absorbent, such as CaO or $CaCO_3$, widely used currently in the industrial field has low solubility to water and shows a low absorption rate, and is disadvantageous in that handling of solid is required. In the case of an amine-based absorbent, it has high absorption ratio to sulfur dioxide but it is present in the form of a salt. Thus, there are problem in that the absorbent may be discharged together upon the desorption of $SO_2$ to cause a loss of absorbent, the desorbed gas may be contaminated with the absorbent to cause degradation of purity, and amine may be decomposed irreversibly due to the strong binding between amine and $SO_2$.

As a method for overcoming the above-mentioned disadvantages of the amine-based absorbent, there have been continuous attempts to use a room-temperature ionic liquid as a sulfur dioxide absorbent. The solubility of the gas absorbed by the ionic liquid is varied depending on a degree of interaction between the gas and ionic liquid. Thus, it is possible to control the solubility to a specific gas by modifying the cation and anion of the ionic liquid so that the polarity, acidity, basicity and nucleophilicity of the ionic liquid may be adjusted. However, such ionic liquids have some problems, since they are susceptible to moisture and decomposed with ease, they show a low $SO_2$ absorption ratio, and they are too expensive to be used in general applications. In addition, some ionic liquids require a high desorption temperature due to excessively strong binding with $SO_2$, and thus has a problem of a difficulty in regeneration thereof.

According to the present disclosure, there is provided an amine salt compound with an ionic structure having high cost-efficiency, high durability and excellent $SO_2$ absorption ratio in order to overcome the above-mentioned problems related with the conventional ionic liquids. After studying the problems of the conventional amine-based ionic liquids and the sulfur dioxide absorption mechanism intensively, it has been found that use of a molten salt including a hydroxyl group-containing diamine-based cation and an anion, more particularly a molten salt having a compound structure selected from the following [Chemical Formula 1] to [Chemical Formula 3], allows not only reversible collection of a significantly low concentration of $SO_2$ but also selective removal of $SO_2$ even in the presence of a large amount of $CO_2$.

Hereinafter, the present disclosure will be explained in detail.

The sulfur dioxide and sulfurous acid absorbent according to the present disclosure is selected from the group consisting of the following [Chemical Formula 1] to [Chemical Formula 3]:

[Chemical Formula 1]

[Chemical Formula 2]

[Chemical Formula 3]

In Chemical Formula 1 to Chemical Formula 3, $R_1$-$R_4$ are the same or different and each is independently selected from the group consisting of H, a C1-C6 alkyl, carbonyl and a C1-C6 alkoxy; X is selected from the group consisting of Cl, Br, I, $MeSO_3$, $CF_3SO_3$, $CF_3CO_2$, $HCO_2$, $CF_3CO_2$ and $CH_3CO_2$; and n is an integer of 1-10.

Particularly, the compound selected from the group consisting of the following [Chemical Formula 1] to [Chemical Formula 3] may be selected from the group consisting of the following [Chemical Formula 4] to [Chemical Formula 11]:

[Chemical Formula 4]

[Chemical Formula 5]

[Chemical Formula 6]

-continued

[Chemical Formula 7]

[Chemical Formula 8]

[Chemical Formula 9]

[Chemical Formula 10]

[Chemical Formula 11]

In addition, the sulfur dioxide and sulfurous acid absorbent according to the present disclosure is obtained through a step of forming a salt of a diamine compound substituted with a hydroxyl group. According to an embodiment, the absorbent is obtained by a method including a step of mixing a compound represented by the following [Chemical Formula 12] with a compound represented by the following [Chemical Formula 15] at a molar ratio of 1:1-5, preferably 1:1-3, to form a salt.

According to another embodiment, the absorbent is obtained by a method including a step of mixing a compound represented by the following [Chemical Formula 13] with a compound represented by the following [Chemical Formula 15] at a molar ratio of 1:1-5, preferably 1:1-3, to form a salt. According to still another embodiment, the absorbent is obtained by a method including a step of mixing a compound represented by the following [Chemical Formula 14] with a compound represented by the following [Chemical Formula 15] at a molar ratio of 1:1-5, preferably 1:1-3, to form a salt.

[Chemical Formula 12]

[Chemical Formula 13]

[Chemical Formula 14]

$Y_1$—$(CH_2)nOH$

[Chemical Formula 15]

In Chemical Formula 12 to Chemical Formula 15, $R_1$-$R_4$ are the same or different and each is independently selected from the group consisting of H, a C1-C6 alkyl, carbonyl and a C1-C6 alkoxy; $Y_1$ is selected from the group consisting of Cl, Br and I; and n is an integer of 1-10.

When the molar ratio is not within the above-defined range in forming the salt compound, a large amount of products other than the desired salt compound may be produced and side reactions may occur frequently to cause a decrease in yield.

It is possible to obtain a compound selected from the group consisting of the above [Chemical Formula 1] to [Chemical Formula 3] by optionally exchanging the anion of the salt compound after the completion of the reaction. For example, the anion of the salt compound after the completion of the reaction is a halogen anion. When the halogen anion is exchanged with another anion, the salt compound is allowed to react with a compound represented by the following [Chemical Formula 16]:

$MY_2$     [Chemical Formula 16]

In Chemical Formula 16, M is selected from the group consisting of Li, K and Na; and $Y_2$ is selected from the group consisting of $MeSO_3$, $CF_3SO_3$, $CF_3CO_2$, $HCO_2$, $CF_3CO_2$ and $CH_3CO_2$.

The absorbent according to the present disclosure is an ionic liquid, and can absorb $SO_2$ in the absence of water when removing $SO_2$ from exhaust gas. However, the absorbent according to the present disclosure can remove $SO_2$ in the presence of water. When removing $SO_2$ in the absence of water, the tertiary amine of the absorbent can absorb $SO_2$ through the physical interaction with $SO_2$. In addition, in the presence of water, $SO_2$ reacts with water first and is present as $H_2SO_3$. Then, $H_2SO_3$, which is a strong acid, reacts with the tertiary amine group of the absorbent so that it may be converted into the structure of $[R_3NH^+][HSO_3^-]$. Herein, when using the ionic liquid (absorbent) according to the present disclosure, the absorbent is isolated after the reaction, and then is heated to 100° C. or more. Thus, it is possible to regenerate the absorbed liquid at a relatively low temperature.

Desorption of $SO_2$ absorbed to the ionic liquid according to the present disclosure requires significantly lower energy as compared to the high-temperature stripping step required for recovery of $SO_2$ in a process using an amine absorbent. This is because removal of $SO_2$ from the ionic liquid to which $SO_2$ is absorbed through physical interaction is significantly easier than removal of $SO_2$ from a primary or secondary amine solution to which $SO_2$ is chemically bound. Particularly, a tertiary amine as a substituent of a quaternary amine group has a significantly lower basicity as compared to a general tertiary amine. Therefore, it shows lower interaction intensity with $SO_2$, which results in a relatively lower regeneration temperature.

In addition, when removing $H_2SO_3$, a structure of $SO_2$ dissolved in water, the resultant $[R_3NH^+][HSO_3^-]$ salt is a weak base-strong acid combination, and thus allows regeneration at a relatively low temperature.

When absorbing $SO_2$ by using the absorbent according to the present disclosure, the absorption temperature is 10-80° C., preferably 30-50° C. When the absorption temperature is lower than 10° C., additional energy may be consumed to reduce the temperature of exhaust gas. When the absorption temperature is higher than 80° C., absorption and desorption may be performed at the same time to cause a decrease in $SO_2$ absorption ratio. The absorption pressure preferably ranges from ambient pressure to 3 atm, considering the vapor pressure (3.44 atm at 21° C.) of $SO_2$.

Further, $SO_2$ desorption temperature is 50-150° C., preferably 70-120° C. When desorption temperature is lower than 50° C., desorption ratio may be decreased. When desorption temperature is higher than 150° C., higher energy is required. Thus, it is preferred to maintain the above-defined temperature range. When absorbing $SO_2$, $SO_2$ absorption is increased as the temperature is decreased and the pressure is increased. Particularly, when absorption pressure is increased, $SO_2$ absorption is increased in almost linearly proportion to the pressure. However, since $SO_2$ partial pressure is not high in most of the processes requiring removal of $SO_2$, it is preferred to use an ionic liquid having a high $SO_2$ absorption ratio even at low pressure.

The examples and experiments will now be described. The following examples and experiments are for illustrative purposes only and not intended to limit the scope of this disclosure. In addition, it will be apparent to those skilled in the art that various changes and modifications may be made based on the disclosure of the present invention including the following examples, and the changes and modifications are also within the scope of the present disclosure as defined in the following claims.

Example 1. Synthesis of Compound Represented by [Chemical Formula 11]

Figure 1:
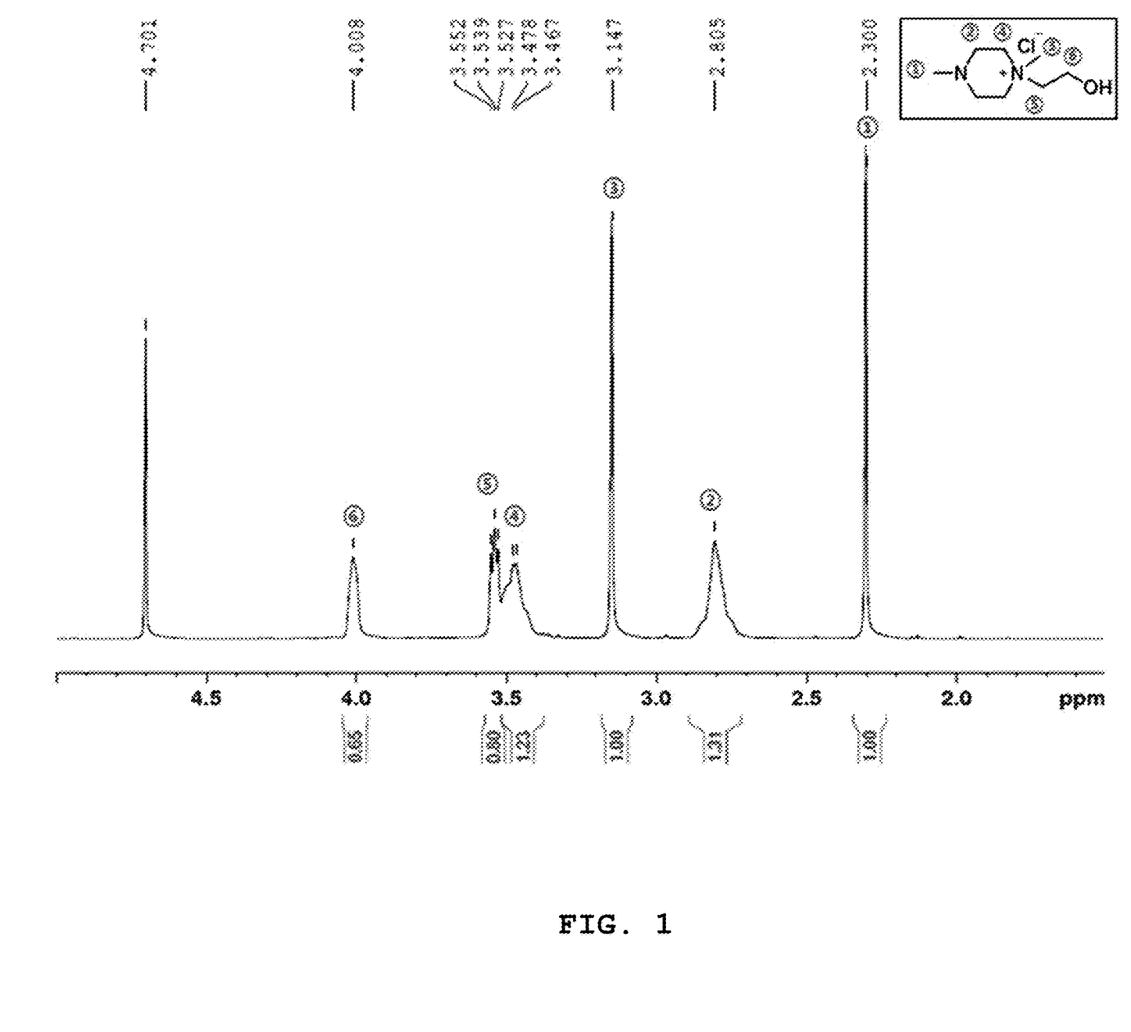
FIG. 1 shows NMR data determined for the molten salt prepared according to Example 1.

Dimethyl piperazine (87.57 mmol, 10.00 g) and hydroxyethyl chloride (87.57 mmol, 7.05 g) were mixed at a molar ratio of 1:1 in $CH_3CN$ (40 mL) as a solvent and reaction was carried out at 100° C. for 24 hours. After the reaction, the remaining hydroxyethyl chloride was removed through extraction with diethyl ether, and then the solvent was removed by using a vacuum pump to obtain a compound of [Chemical Formula 11] (yield 85.20%) (FIG. 1).

Example 2. Synthesis of Compound Represented by [Chemical Formula 4]

N,N,N',N'-tetraethylethylenediamine (58.0 mmol, 10.0 g) and 2-bromoethanol (46.4 mmol. 5.8 g) were used in the same manner as Example 1, except that reaction was carried out at room temperature for 10 hours. In this manner, a compound of [Chemical Formula 4] was obtained (yield 80.3%) (ratio 1:0.8).

$^1$H NMR (300 MHz, DMSO) δ=1.15 (t, 6H), 1.25 (t, 6H), 2.80 (t, 2H), 3.01 (m, 4H), 3.28-3.34 (m, 6H), 3.43 (t, 2H), 3.97 (t, 2H).

Example 3. Synthesis of Compound Represented by [Chemical Formula 5]

N,N'-dibutylpiperazine (50.4 mmol, 10 g) and 4-iodobutanol (40.3 mmol, 8.1 g) were used in the same manner as Example 1, except that reaction was carried out at room temperature for 10 hours. In this manner, a compound represented by [Chemical Formula 5] was obtained (yield 85.6%).

$^1$H NMR (300 MHz, DMSO) δ=0.89-0.91 (m, 6H), 1.29-1.52 (m, 8H), 1.71 (m, 4H), 2.80 (t, 6H), 3.01 (t, 2H), 3.22 (t, 4H), 3.34 (t, 4H), 3.46 (t, 2H).

Example 4. Synthesis of Compound Represented by [Chemical Formula 6]

1,4-diazabycyclo[2.2.2]octane (89 mmol, 10 g) and 2-bromoethanol (71.2 mmol, 8.9 g) were allowed to react at room temperature for 24 hours in the same manner as Example 1. After the reaction, the remaining 1,4-diazabycyclo[2.2.2]octane and 2-bromoethanol were removed through extraction with diethyl ether. Then, sodium trifluoroacetate (64 mmol, 8.7 g) was added and the resultant mixture was agitated at room temperature for 12 hours. After the reaction, the resultant salt was removed by filtration and the solvent was removed by using a vacuum pump to obtain a compound of [Chemical Formula 6] (yield 70%).

$^1$H NMR (300 MHz, DMSO) δ=2.80 (t, 6H), 3.34-3.43 (m, 8H), 3.97 (t, 2H).

Example 5. Synthesis of Compound Represented by [Chemical Formula 7]

N,N-dimethyl-N-hydroxyethylpiperazium chloride (50 mmol, 9.7 g) obtained from Example 1 was allowed to react with $CF_3SO_3Na$ (50 mmol, 8.6 g) in the presence of $CH_3CN$ as a solvent at room temperature for 12 hours. After the reaction, the formed NaCl was removed by filtration and the solvent was removed by using a vacuum pump to obtain a compound of [Chemical Formula 7] (yield 95%).

$^1$H NMR (300 MHz, DMSO) δ=2.19 (s, 3H), 2.77-2.82 (t, 4H), 3.28-3.36 (m, 7H), 3.41-3.45 (t, 2H), 3.95-4.00 (t, 2H).

Example 6. Synthesis of Compound Represented by [Chemical Formula 8]

N,N-dimethyl-N-hydroxyethylpiperazium chloride (50 mmol, 9.7 g) obtained from Example 1 was allowed to react with $HCO_2Na$ (50 mmol, 3.4 g) in the presence of $CH_3CN$ as a solvent at room temperature for 12 hours. After the reaction, the formed NaCl was removed by filtration and the solvent was removed by using a vacuum pump to obtain a compound of [Chemical Formula 8] (yield 96%).

$^1$H NMR (300 MHz, DMSO) δ=2.18 (s, 3H), 2.78-2.82 (t, 4H), 3.28-3.37 (m, 7H), 3.42-3.46 (t, 2H), 3.95-3.99 (t, 2H).

Example 7. Synthesis of Compound Represented by [Chemical Formula 9]

N,N-dimethyl-N-hydroxyethylpiperazium chloride (50 mmol, 9.7 g) obtained from Example 1 was allowed to react with $CH_3CO_2Na$ (50 mmol, 4.1 g) in the presence of $CH_3CN$ as a solvent at room temperature for 12 hours. After the reaction, the formed NaCl was removed by filtration and the solvent was removed by using a vacuum pump to obtain a compound of [Chemical Formula 9] (yield 96%).

$^1$H NMR (300 MHz, DMSO) δ=2.10 (s, 3H), 2.18 (s, 3H), 2.78-2.82 (t, 4H), 3.28-3.36 (m, 7H), 3.41-3.45 (t, 2H), 3.95-3.99 (t, 2H).

Example 8. Synthesis of Compound Represented by [Chemical Formula 10]

N,N-dimethyl-N-hydroxyethylpiperazium chloride (50 mmol, 9.7 g) obtained from Example 1 was allowed to react with $CF_3CO_2Na$ (50 mmol, 6.6 g) in the presence of $CH_3CN$ as a solvent at room temperature for 12 hours. After the reaction, the formed NaCl was removed by filtration and the solvent was removed by using a vacuum pump to obtain a compound of [Chemical Formula 10] (yield 97%).

$^1$H NMR (300 MHz, DMSO) δ=2.18 (s, 3H), 2.80 (s, 4H), 3.30-3.34 (m, 7H), 3.43 (t, 2H), 3.97 (t, 2H), 4.24 (s, H).

TEST EXAMPLES

Test Example 1. Determination of $SO_2$ Absorption

Figure 2:
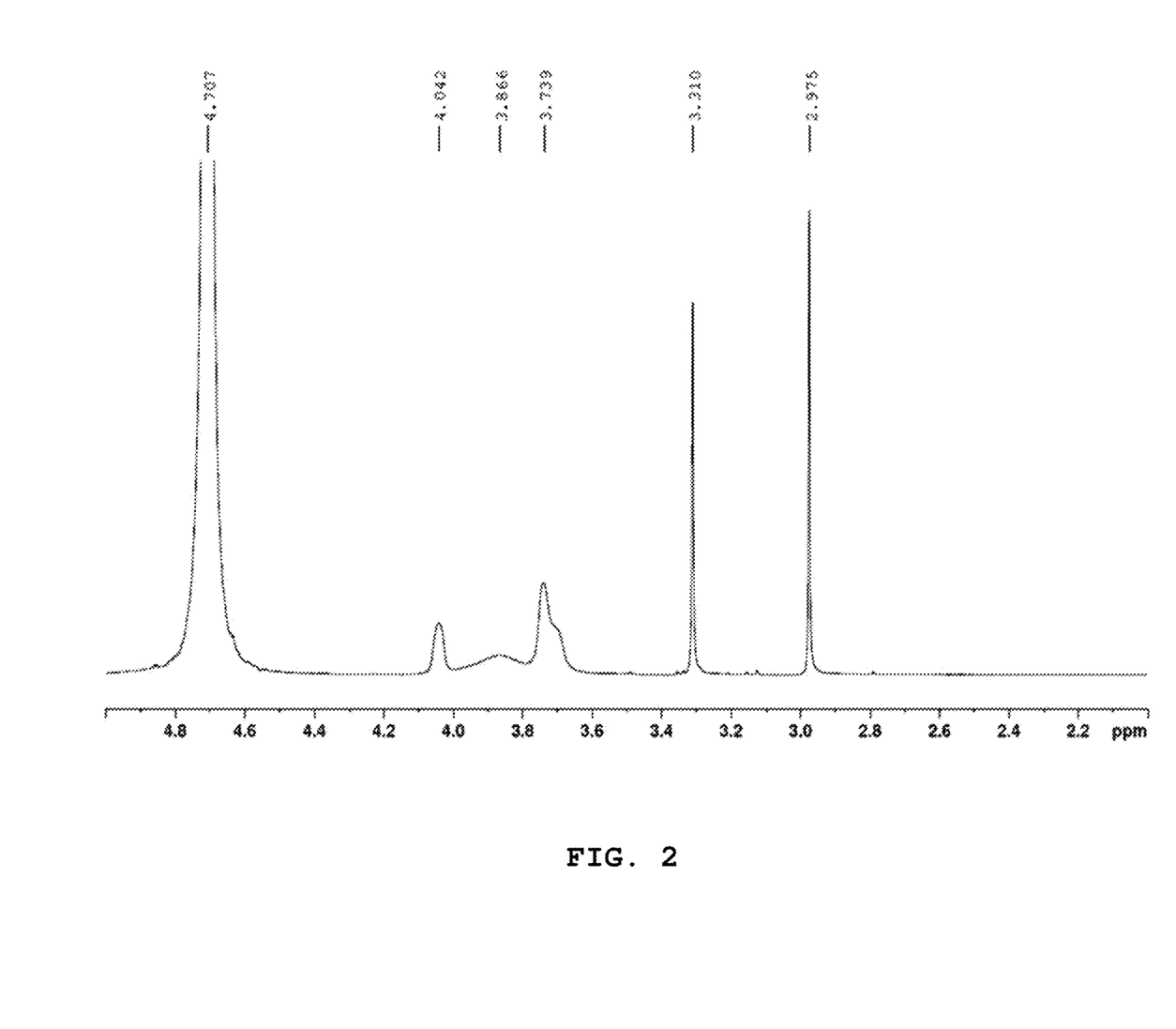
FIG. 2 shows NMR data of the ionic liquid prepared from the molten salt according to Example 1 after the reaction with $SO_2$.
Figure 7:
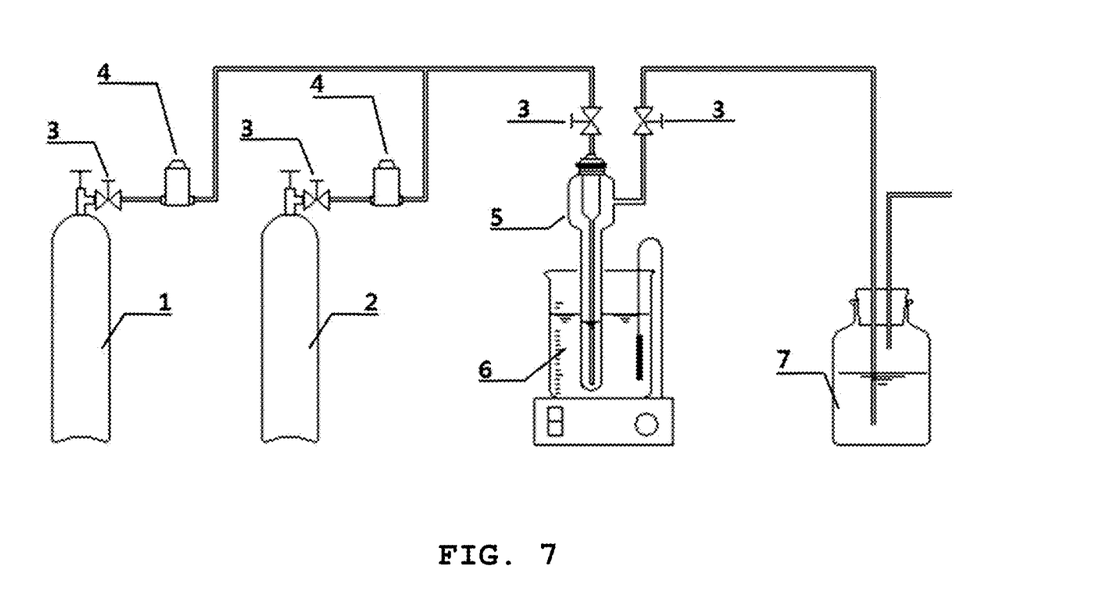
FIG. 7 shows an absorption reactor.

In the absorption reactor R1 as shown in FIG. 7, 0.5 g of each of the molten salts according to Examples 1-8 was dissolved into 4.5 g of water and the following $SO_2$ absorption test was carried out, while the temperature of the thermostat was maintained at 30° C. After the storage cylinder 2 was filled with $SO_2$ under 3 atm, an increase in weight was measured as a function of time while allowing $SO_2$ to flow at a 30 cc/min by using a mass flow controller. After 60 minutes, the weight was not increased any more. At that time, the amount of $SO_2$ dissolved in the ionic liquid was calculated. Herein, NMR data obtained after the reaction of the ionic liquid obtained from the molten salt according to Example 1 with $SO_2$ are shown in FIG. 2.

TABLE 1

| | Structure | $SO_2$ absorption (gmole-$SO_2$/gmole-absorbent) |
|---|---|---|
| Example 1 [Chemical Formula 11] | (structure with $Cl^-$, piperazinium, $-CH_2CH_2OH$) | 1.15 |
| Example 2 [Chemical Formula 4] | (structure with $Br^-$, triethylamine/ammonium, $CH_2CH_2OH$) | 1.08 |
| Example 3 [Chemical Formula 5] | (structure with $I^-$, piperazinium, $C_4H_9$, $(CH_2)_4OH$) | 1.14 |
| Example 4 [Chemical Formula 6] | (structure with $CF_3CO_2^-$, DABCO, $-(CH_2)_2OH$) | 1.05 |
| Example 5 [Chemical Formula 7] | (structure with $CF_3SO_3^-$, piperazinium, $CH_3$, $(CH_2)_2OH$) | 0.99 |
| Example 6 [Chemical Formula 8] | (structure with $HCO_2^-$, piperazinium, $CH_3$, $(CH_2)_2OH$) | 1.03 |
| Example 7 [Chemical Formula 9] | (structure with $CH_3CO_2^-$, piperazinium, $CH_3$, $(CH_2)_2OH$) | 1.20 |
| Example 8 [Chemical Formula 10] | (structure with $CF_3CO_2^-$, piperazinium, $CH_3$, $(CH_2)_2OH$) | 1.11 |

As shown in Table 1, the ionic liquid obtained from the molten salt according to Examples 1-8 shows improved $SO_2$ absorption as compared to the conventional absorbent.

Test Example 2. Determination of $SO_2$ Absorption Depending on Absorption Temperature The $SO_2$ absorption test was carried out in the same manner as Test Example 1 by using the ionic liquid obtained from the molten salt according to Example 1, setting the pressure at 1 atm and varying the absorption temperature to 20, 40, 50 and 60° C. The results are shown in the following Table 2.

TABLE 2

| Absorption temperature (° C.) | $SO_2$ Absorption (gmole-$SO_2$/gmole-absorbent) |
|---|---|
| 20 | 2.1 |
| 40 | 1.15 |
| 50 | 1.13 |
| 60 | 0.85 |

As shown in Table 2, the ionic liquid obtained from the molten salt according to Example 1 shows a gradual decrease in $SO_2$ absorption, as the absorption temperature is increased.

Test Example 3. $SO_2$ Absorption and Desorption

Figure 3:
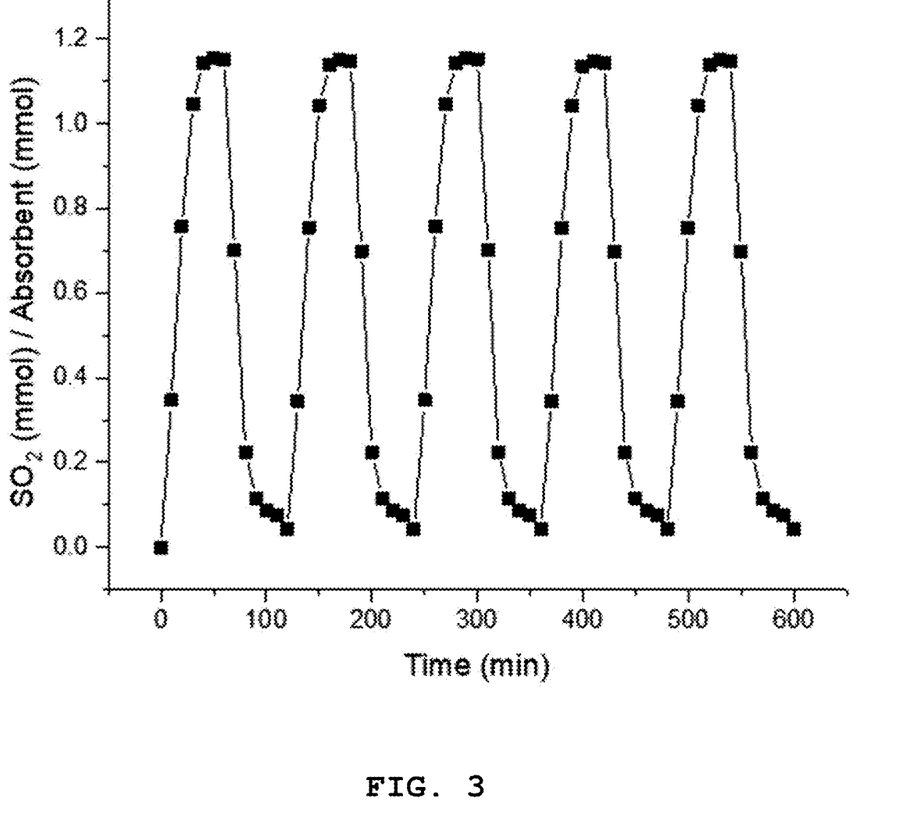
FIG. 3 is a graph illustrating the results of repeating $SO_2$ absorption and desorption 4 times by using the ionic liquid prepared from the molten salt according to Example 1.

The $SO_2$ absorption was determined in the same manner as Test Example 1 by using the ionic liquid obtained from the molten salt according to Example 1, and setting the pressure at 1 atm and the absorption temperature to 30° C. Then, the reactor was purged with nitrogen at 10 mL/min to desorb $SO_2$. After completing the first cycle of $SO_2$ absorption and desorption, absorption/desorption was repeated four times under the same condition. The absorption/desorption tendency is shown in FIG. 3. Herein, after carrying out absorption/desorption five times, NMR data are shown in FIG. 4.

Figure 4:
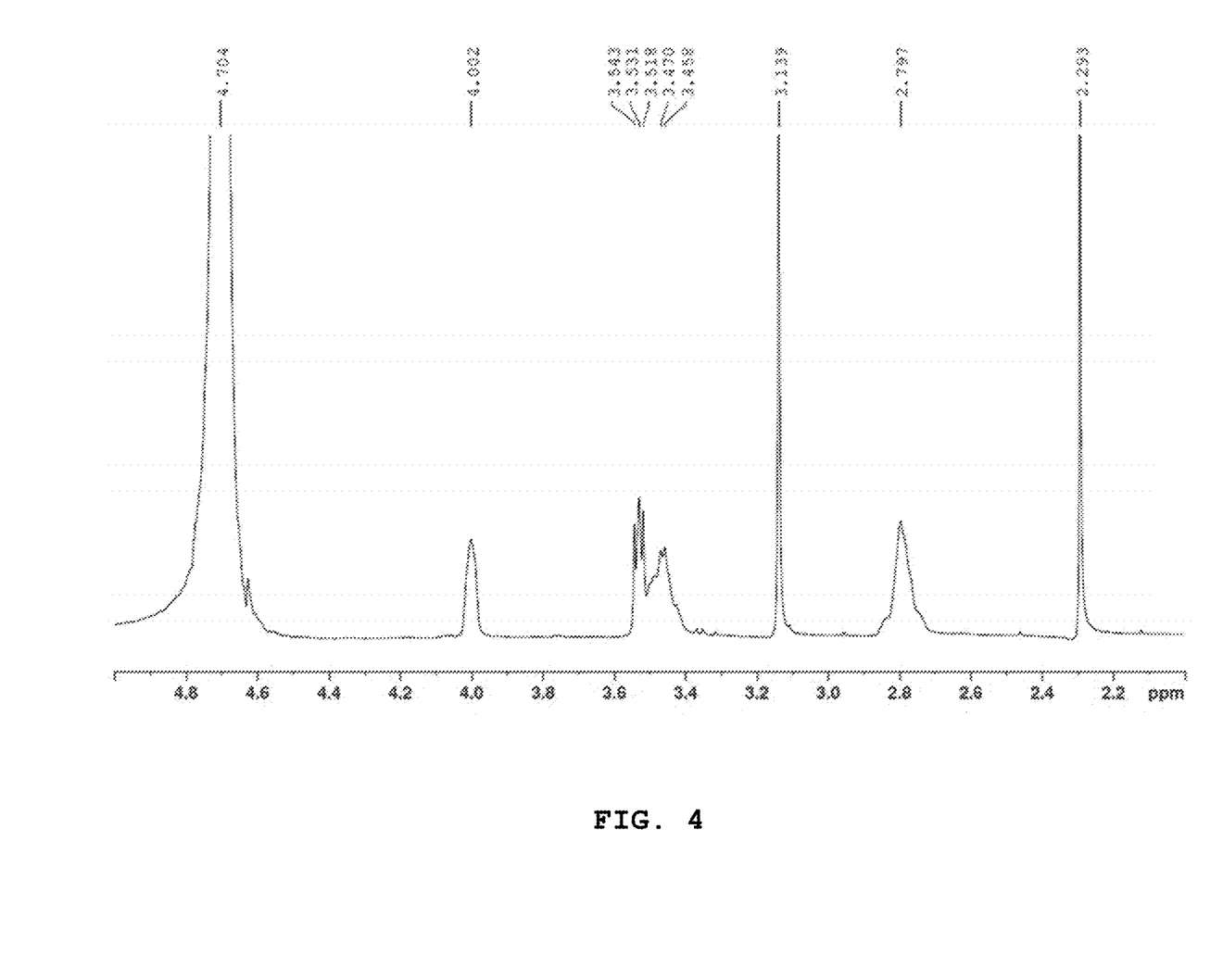
FIG. 4 shows NMR data illustrating the results of repeating $SO_2$ absorption and desorption 5 times by using the ionic liquid prepared from the molten salt according to Example 1.

As shown in FIG. 3 and FIG. 4, the ionic liquid according to the present disclosure maintains absorbability/desorbability similar to that of the first cycle even after being used repeatedly (FIG. 3). When comparing the NMR data (FIG. 4) after repeating absorption/desorption five times with the NMR data (FIG. 1) of the molten salt according to Example 1 before carrying out absorption/desorption, it can be seen that the molten salt shows no change in structure even after repeating absorption/desorption.

Test Example 4. Determination of $SO_2$ Concentration Emitted when Using Gas Containing High-Concentration $SO_2$ An absorption test was carried out by using gas containing 1000 ppm of $SO_2$ and the ionic liquid obtained from the molten salt according to Example 1 in the $SO_2$ absorption-desorption system.

Figure 5:
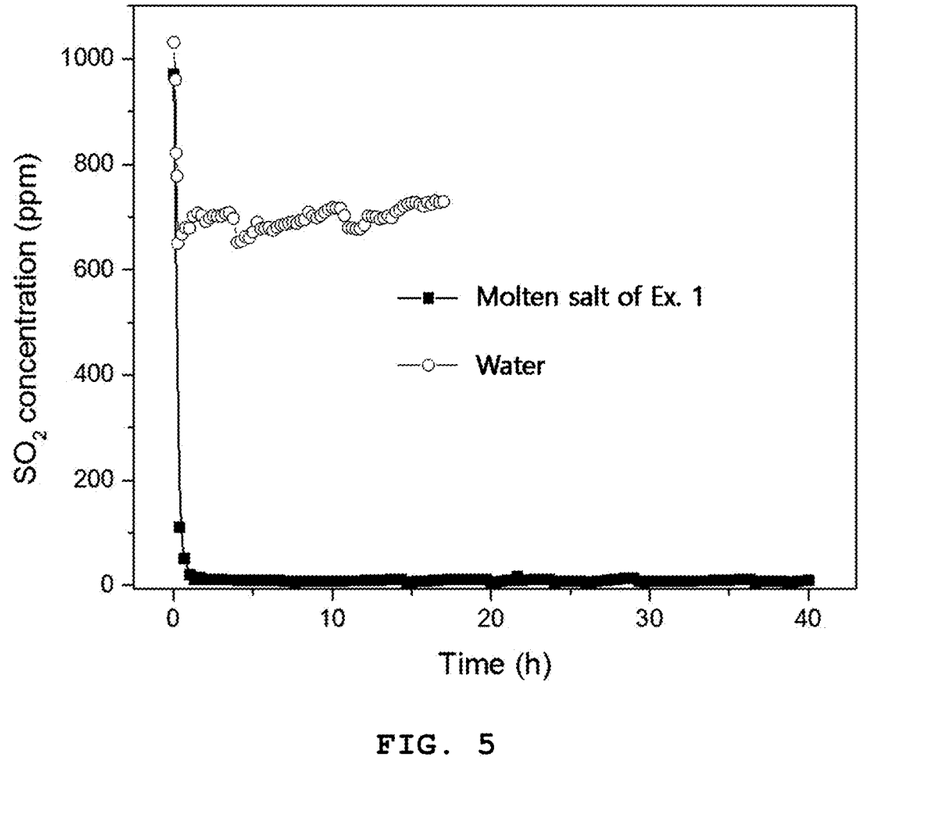
FIG. 5 is a graph illustrating the $SO_2$ concentration obtained when the ionic liquid prepared from the molten salt according to Example 1 or water is applied to a $SO_2$ absorption-desorption system in the presence of gas containing $SO_2$ at a high concentration.

FIG. 5 is a graph illustrating the $SO_2$ concentration obtained when the ionic liquid prepared from the molten salt according to Example 1 or water is applied to a $SO_2$ absorption-desorption system in the presence of gas containing $SO_2$ at a high concentration.

As shown in FIG. 5, when using water instead of the ionic liquid according to Example 1, about 700 ppm of $SO_2$ is emitted. On the contrary, when using the ionic liquid according to Example 1, about 10 ppm of $SO_2$ is emitted, suggesting a significant decrease in concentration of discharged $SO_2$. Thus, it can be seen that $SO_2$ is removed at a ratio of 98.8%.

Test Example 5. Determination of Solidification Depending on Presence of Hydroxyl Group FIG. 6A shows a photographic image taken after the reaction of the ionic liquid containing a different concentration of hydroxyl group-free diamine salt with $SO_2$, and FIG. 6B shows a photographic image taken after the reaction of the ionic liquid containing a different concentration of the molten salt according to Example 1 with $SO_2$.

Figure 6A:
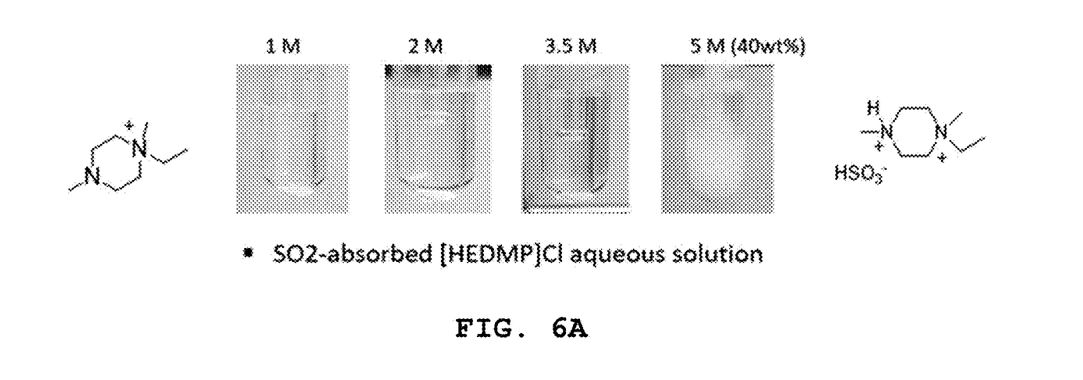
FIG. 6A shows a photographic image taken after the reaction of the ionic liquid containing a different concentration of hydroxyl group-free diamine salt with $SO_2$.
Figure 6B:
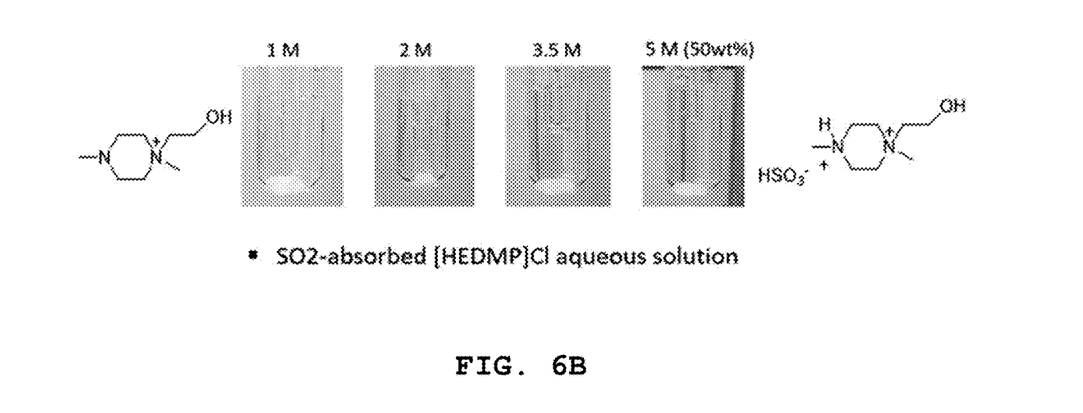
FIG. 6B shows a photographic image taken after the reaction of the ionic liquid containing a different concentration of the molten salt according to Example 1 with $SO_2$.

As shown in FIG. 6A and FIG. 6B, after absorbing $SO_2$ by using an aqueous solution containing 5 M of a diamine-based salt having no hydroxyl group, the ionic liquid is solidified by absorbing $SO_2$ (FIG. 6A). Such precipitation of salt may cause a phenomenon, such as pipe blockage, during a process for absorbing and separating $SO_2$.

On the contrary, when using the ionic liquid containing 5 M of the molten salt having a hydroxyl group according to Example 1, the ionic liquid maintains a liquid state after absorbing $SO_2$ (FIG. 6B).

Test Example 6. Determination of Carbon Dioxide Absorption

An absorption test was carried out in the same manner as Test Example 1 by using the ionic liquid obtained from the molten salt according to Example 1, except that $CO_2$ gas was introduced instead of $SO_2$. After determining the absorbed amount, no $CO_2$ absorption occurred and the ionic liquid showed no change in NMR. This suggests that the ionic liquid obtained from the molten salt selectively interacts with $SO_2$.

Therefore, it is possible to absorb a small amount of $SO_2$ under the atmosphere of exhaust gas containing $CO_2$ at a high concentration.

| [Description of Drawing Numerals] | |
|---|---|
| 1: Nitrogen cylinder | 2: $SO_2$ cylinder |
| 3: Valve | 4: Mass flow controller |
| 5: Absorbent container | 6: Silicone oil bath |
| 7: NaOH solution | |

What is claimed is:

1. A sulfur dioxide absorbent that is an ionic liquid which absorbs sulfur dioxide and sulfurous acid ($H_2SO_3$), comprising:
   a solvent; and
   a salt of a diamine compound that is substituted with a hydroxyl group, that has a chemical formula selected from the group consisting of Chemical Formula 1 to 3 below, and that is dissolved in the solvent:

Chemical Formula 1

Chemical Formula 2

Chemical Formula 3 where, in Chemical Formula 1 and 2, $R_1$-$R_4$ are the same or different and each is independently selected from the group consisting of H, a C1-C6 alkyl group, and a C1-C6 alkoxy group; and where, in Chemical Formula 1 to 3, X is selected from the group consisting of Cl, Br, I, $MeSO_3$, $CF_3SO_3$, $HCO_2$, $CF_3CO_2$ and $CH_3CO_2$; and n is an integer of 1-10.

2. The sulfur dioxide absorbent according to claim 1, wherein the sulfur dioxide absorbent selectively absorbs sulfur dioxide and sulfurous acid ($H_2SO_3$) formed by combination of sulfur dioxide with water but not $CO_2$.

3. The sulfur dioxide absorbent according to claim 1, wherein the sulfur dioxide absorbent has an absorption temperature that ranges from 10-80° C.

4. The sulfur dioxide absorbent according to claim 1, wherein the sulfur dioxide absorbent has a desorption temperature that ranges from 50-150° C.

5. The sulfur dioxide absorbent according to claim 1, wherein the sulfur dioxide absorbent is selected from the group consisting of Chemical Formula 4 to 11 below:

Chemical Formula 4

Chemical Formula 5

Chemical Formula 6

Chemical Formula 7

Chemical Formula 8

Chemical Formula 9

-continued

Chemical Formula 10

$$\text{CF}_3\text{CO}_2^-$$

H₃C—N⌒N⁺(CH₃)(CH₂)₂OH, and

Chemical Formula 11

Cl⁻

—N⌒N⁺(CH₃)(CH₂CH₂OH).

6. The sulfur dioxide absorbent according to claim 1, wherein the chemical formula is Chemical Formula 2.

7. The sulfur dioxide absorbent according to claim 1, wherein the chemical formula is Chemical Formula 2 and X is Cl, Br, or I.

8. A sulfur dioxide absorbent that is an ionic liquid which absorbs sulfur dioxide and sulfurous acid ($H_2SO_3$), comprising:
   a solvent; and
   a salt of a diamine compound that is substituted with a hydroxyl group, that has a chemical formula selected from the group consisting of Chemical Formula 1 to 3 below, and that is dissolved in the solvent:

Chemical Formula 1

$$R_1\text{-N}(R_2)\text{-CH}_2\text{CH}_2\text{-N}^+(R_3)(R_4)(CH_2)_n\text{OH}, \quad X^-$$

Chemical Formula 2

$$R_2\text{—N}⌒\text{N}^+(R_1)(CH_2)_n\text{OH}, \quad X^-$$ and

Chemical Formula 3

$$N⌒N^+—(CH_2)_n\text{OH}, \quad X^-$$

where, in Chemical Formula 1 and 2, $R_1$-$R_4$ are the same or different and each is independently selected from the group consisting of H, a C1-C6 alkyl group, and a C1-C6 alkoxy group; and where, in Chemical Formula 1 to 3, X is selected from the group consisting of Cl, Br, I, $CF_3SO_3$, and $CF_3CO_2$; and n is an integer of 1-10.

9. The sulfur dioxide absorbent according to claim 8, wherein the sulfur dioxide absorbent is selected from the group consisting of Chemical Formula 4 to 7, 10, and 11 below:

Chemical Formula 4

$$Et_2N\text{-CH}_2\text{CH}_2\text{-N}^+(Et)_2\text{CH}_2\text{CH}_2\text{OH}, \quad Br^-$$

Chemical Formula 5

I⁻

$$C_4H_9\text{—N}⌒\text{N}^+(C_4H_9)(CH_2)_4\text{OH},$$

Chemical Formula 6

$$\text{CF}_3\text{CO}_2^-$$

N⌒N⁺—(CH₂)₂OH,

Chemical Formula 7

$$\text{CF}_3\text{CO}_2^-$$

H₃C—N⌒N⁺(CH₃)(CH₂)₂OH,

Chemical Formula 10

$$\text{CF}_3\text{CO}_2^-$$

H₃C—N⌒N⁺(CH₃)(CH₂)₂OH, and

Chemical Formula 11

Cl⁻

—N⌒N⁺(CH₃)(CH₂CH₂OH).

10. The sulfur dioxide absorbent according to claim 8, wherein the sulfur dioxide absorbent selectively absorbs sulfur dioxide and sulfurous acid ($H_2SO_3$) formed by combination of sulfur dioxide with water but not $CO_2$.

11. The sulfur dioxide absorbent according to claim 8, wherein the sulfur dioxide absorbent has an absorption temperature that ranges from 10-80° C.

12. The sulfur dioxide absorbent according to claim 8, wherein the sulfur dioxide absorbent has a desorption temperature that ranges from 50-150° C.

13. The sulfur dioxide absorbent according to claim 8, wherein the chemical formula is Chemical Formula 2.

14. The sulfur dioxide absorbent according to claim 8, wherein the chemical formula is Chemical Formula 2 and X is Cl, Br, or I.

15. A sulfur dioxide absorbent that is an ionic liquid which absorbs sulfur dioxide and sulfurous acid ($H_2SO_3$), comprising:
   a solvent; and
   a salt of a diamine compound that is substituted with a hydroxyl group, that has Chemical Formula 2 below, and that is dissolved in the solvent:

Chemical Formula 2

$$R_2\text{—N}⌒\text{N}^+(R_1)(CH_2)_n\text{OH}, \quad X^-$$

where $R_1$ and $R_2$ are the same or different and each is independently selected from the group consisting of H, a C1-C6 alkyl group, and a C1-C6 alkoxy group, X is chlorine (Cl), and n is an integer of 1-10.

16. The sulfur dioxide absorbent according to claim 15, wherein the sulfur dioxide absorbent selectively absorbs sulfur dioxide and sulfurous acid ($H_2SO_3$) formed by combination of sulfur dioxide with water but not $CO_2$.

17. The sulfur dioxide absorbent according to claim 15, wherein the sulfur dioxide absorbent has an absorption temperature that ranges from 10-80° C.

18. The sulfur dioxide absorbent according to claim 15, wherein the sulfur dioxide absorbent has a desorption temperature that ranges from 50-150° C.

* * * * *